United States Patent
Song et al.

(10) Patent No.: US 10,481,348 B2
(45) Date of Patent: Nov. 19, 2019

(54) OPTICAL SYSTEM FOR COUPLING LIGHT INTO A WAVEGUIDE

(71) Applicant: miDiagnostics NV, Leuven (BE)

(72) Inventors: Jeonghwan Song, Leuven (BE); Pol Van Dorpe, Leuven (BE); Giuseppe Fiorentino, Leuven (BE); Philippe Soussan, Leuven (BE); Xavier Rottenberg, Leuven (BE)

(73) Assignee: miDiagnostics NV, Leuven (BE)

( * ) Notice: Subject to any disclaimer, the term of this patent is extended or adjusted under 35 U.S.C. 154(b) by 0 days.

(21) Appl. No.: 15/689,966

(22) Filed: Aug. 29, 2017

(65) Prior Publication Data
US 2018/0074271 A1   Mar. 15, 2018

(30) Foreign Application Priority Data
Sep. 9, 2016 (EP) .................................... 16188051

(51) Int. Cl.
*G02B 6/42* (2006.01)
*G01N 15/14* (2006.01)
(Continued)

(52) U.S. Cl.
CPC .......... *G02B 6/4214* (2013.01); *G01N 15/14* (2013.01); *G01N 33/483* (2013.01); *G02B 6/34* (2013.01);
(Continued)

(58) Field of Classification Search
CPC .... G02B 6/4214; G02B 6/4206; G01N 15/14; G01N 33/483
See application file for complete search history.

(56) References Cited

U.S. PATENT DOCUMENTS 3,883,221 A * 5/1975 Rigrod .................... G02B 6/34
                                              385/36
4,525,034 A * 6/1985 Simmons ............. G02B 5/3066
                                              359/485.02
(Continued)

FOREIGN PATENT DOCUMENTS

CN   103837937 A   6/2014
JP   H01107212 A   4/1989

OTHER PUBLICATIONS

K.S. Kaur, A.Z. Subramanian, P. Cardile, R. Verplancke, J. Van Kerrebrouck, S. Spiga, R. Meyer, J. Bauwelinck, R. Baets, and G. Van Steenberge, "Flip-chip assembly of VCSELs to silicon grating couplers via laser fabricated SU8 prisms," Opt. Express 23, 28264-28270 (2015).*

(Continued)

*Primary Examiner* — Peter Radkowski
(74) *Attorney, Agent, or Firm* — Hodgson Russ LLP (57) ABSTRACT

There is provided an optical system for coupling light into a waveguide. The optical system comprising a coupler arranged at a portion of the waveguide. The coupler has a surface with a grating structure for directing light into the waveguide formed therein. A cladding layer embeds the coupler and an optical path changing structure is formed in the cladding layer. The optical path changing structure has a refractive surface and a reflective surface, each forming an acute angle with respect to the surface of the coupler. Light which enters the optical path changing structure through the refractive surface will be refracted and directed towards the reflective surface. The reflective surface is arranged to reflect the light such that it is directed towards the grating structure of the coupler along a direction suitable for efficient coupling of light into the waveguide.

13 Claims, 5 Drawing Sheets

(51) Int. Cl.
  G01N 33/483 (2006.01)
  G02B 6/34 (2006.01)
  G01N 15/00 (2006.01)
  G02B 6/124 (2006.01)
  G02B 6/12 (2006.01)

(52) U.S. Cl.
  CPC ... G02B 6/4206 (2013.01); *G01N 2015/0065* (2013.01); *G01N 2015/1486* (2013.01); *G02B 6/124* (2013.01); *G02B 2006/12107* (2013.01); *G02B 2006/12114* (2013.01)

(56) References Cited

U.S. PATENT DOCUMENTS

| | | | | |
|---|---|---|---|---|
| 4,578,793 | A * | 3/1986 | Kane | H01S 3/0606 372/50.1 |
| 4,634,223 | A * | 1/1987 | Ishii | G02B 5/04 359/613 |
| 4,740,986 | A * | 4/1988 | Reeder | H01S 3/115 359/834 |
| 5,101,459 | A * | 3/1992 | Sunagawa | G02B 6/34 385/130 |
| 5,208,882 | A * | 5/1993 | Strasser | G02B 6/124 385/130 |
| 5,363,226 | A * | 11/1994 | Strasser | G02B 6/12007 359/566 |
| 5,495,462 | A * | 2/1996 | Nishiwaki | G02B 6/14 369/112.27 |
| 5,973,864 | A * | 10/1999 | Lehmann | G01J 3/42 359/834 |
| 6,097,555 | A * | 8/2000 | Lehmann | G01J 3/42 359/834 |
| 6,172,823 | B1 * | 1/2001 | Lehmann | G01J 3/42 356/300 |
| 6,271,526 | B1 * | 8/2001 | Cwik | B82Y 20/00 250/371 |
| 2002/0191889 | A1 * | 12/2002 | Lucero | G02B 6/12004 385/16 |
| 2004/0156590 | A1 | 8/2004 | Gunn, III et al. | |
| 2005/0094939 | A1 * | 5/2005 | Ghiron | G02B 6/12007 385/36 |
| 2009/0162013 | A1 * | 6/2009 | Webster | G02B 6/32 385/39 |
| 2009/0290837 | A1 | 11/2009 | Chen et al. | |
| 2015/0362739 | A1 * | 12/2015 | Zambuto | G02B 27/141 359/566 |
| 2016/0062062 | A1 | 3/2016 | Miao et al. | |

OTHER PUBLICATIONS

Alejandro Sanchez-Postigo, J. Gonzalo Wangüemert-Pérez, José Manuel Luque-González, Íñigo Molina-Fernández, Pavel Cheben, Carlos A. Alonso-Ramos, Robert Halir, Jens H. Schmid, and Alejandro Ortega-Moñux, "Broadband fiber-chip zero-order surface grating coupler with 0.4 dB efficiency," Opt. Lett. 41, 3013-3016 (2016).*

Schmid et al., Optimized grating coupler with fully etched slots; Optics Express, V. 17, N. 13, 2009, 11066.*

Yun Wang, Xu Wang, Jonas Flueckiger, Han Yun, Wei Shi, Richard Bojko, Nicolas A. F. Jaeger, and Lukas Chrostowski, "Focusing sub-wavelength grating couplers with low back reflections for rapid prototyping of silicon photonic circuits," Opt. Express 22, 20652-20662 (2014).*

Kaur et al., Flip-chip assembly of VCSELs to silicon grating couplers via laser fabricated SU8 prisms, Nov. 2, 2015 | vol. 23, No. 22 | DOI:10.1364/OE.23.028264 | Optics Express 28268.*

Sanchez-Postigo et al., Broadband fiber-chip zero-order surface grating coupler with 0.4 dB efficiency, vol. 41, No. 13 / Jul. 1, 2016 / Optics Letters.*

Schmid et al., Optimized grating coupler with fully etched slots, Jun. 22, 2009 / vol. 17, No. 13 / Optics Express 11068.*

Wang et al., Design of broadband subwavelength grating couplers with low back reflection,vol. 40, No. 20 / Oct. 15, 2015 / Optics Letters.*

EPO, Office Action for EP Application No. 17188766, dated Feb. 6, 2018.

* cited by examiner

OPTICAL SYSTEM FOR COUPLING LIGHT INTO A WAVEGUIDE

CROSS-REFERENCE TO RELATED APPLICATIONS

This application claims priority to and the benefit of European Patent Application No. 16188051.3, filed on Sep. 9, 2016, the disclosure of which is incorporated herein by reference in its entirety.

TECHNICAL FIELD

The disclosed embodiments relate to optical systems. More specifically, the disclosure relates to an optical system for coupling light into a waveguide.

BACKGROUND

Silicon photonics has emerged as a mature technology platform for applications in optical data communications and telecommunications. High quality photonic integrated circuits (PICs) can today be fabricated with good process control and yield. State-of-the-art devices such as optical waveguides are frequently used on this platform. One useful optical component on these circuits is the nanophotonic waveguide which is used to facilitate optical communication between different optical devices on the circuit.

Nanophotonic waveguides have relatively small physical dimensions. One challenge is therefore to achieve an efficient light coupling into, and out from, the waveguide. One method for coupling light into a waveguide is in-line coupling where the light is coupled into the waveguide directly at one of its ends. The small cross sectional area of the waveguide requires accurate alignment to obtain high coupling efficiency. The coupling efficiency will be strongly dependent on the relative alignment of the components, making in-line coupling unsuitable for many practical applications as these typically require considerably higher tolerance.

One solution to the issue described above is the use of grating coupler embedded platforms. The grating coupler is typically realized by forming a grating structure on top of, or below, a waveguide. The incident light hits the grating at an angle of incidence with respect to the grating. For specific combinations of incident angles and light frequency, there is resonance, allowing the grating to couple light into a guided mode of the waveguide.

For design considerations of the essentially two-dimensional photonic integrated circuits, the grating coupler introduces a challenge as the direction of the incident light is different from the plane of the waveguide (i.e. the plane of the circuit board). To solve this problem, an optical arrangement can be added to deflect the light beam from a direction parallel with the plane of the waveguide (for example at an output of a semiconductor laser), into a direction forming an angle with respect to the waveguide for input to the grating coupler. The grating coupler then alters the direction of the light beam back into a direction in the plane of the waveguide.

In one proposed approach, an incident light beam is initially in the plane of the waveguide. A mirror forming an angle below 45° with respect to the plane of the waveguide is used on top of a grating coupler to deflect the incident light beam such that it hits the grating coupler at an angle of incidence which gives an efficient light coupling. The mirror is part of an additional wave guide attached on top of the grating coupler, making the solution relatively complex. Moreover, the angle below 45° required for efficient light coupling is difficult and relatively expensive to manufacture. For example, the mirror has to be formed by a dicing technique with a fine grid size blaze or patterned with a gray scale mask. There is thus room for improvements.

SUMMARY

According to a first aspect, there is provided an optical system for coupling light into a waveguide, comprising:
a waveguide having a portion for guiding light along a first direction,
a coupler arranged at said portion of the waveguide, wherein the coupler has a surface with a grating structure formed therein for directing light into the waveguide, the surface having a normal which is orthogonal to the first direction, and
a cladding layer embedding the coupler, the cladding layer having an optical path changing structure formed therein, the optical path changing structure having a refractive surface and a reflective surface, each forming an acuteangle with respect to the surface of the coupler,
wherein, for light which enters the optical path changing structure through the refractive surface along a second direction which is orthogonal to said normal, the refractive surface is arranged to refract the light such that it is directed towards the reflective surface along a third direction which is different from the second direction, and
wherein the reflective surface is arranged to reflect the light of the third direction such that it is directed towards the grating structure of the coupler along a fourth direction.

BRIEF DESCRIPTION OF THE DRAWINGS

The above, as well as additional features and advantages, will be better understood through the following illustrative and non-limiting detailed description of several embodiments described herein, with reference to the appended drawings, where the same reference numerals will be used for similar elements, wherein:

FIG. 3a shows schematically a three-dimensional view of the optical system in a back-fire configuration according to example embodiments of the present disclosure.

FIG. 3b shows schematically a top view of the optical system of FIG. 3a

DETAILED DESCRIPTION

Exemplary embodiments provides a way to couple light into a waveguide more efficiently while still keeping manufacturing costs low.

The optical path changing structure of the optical system achieves a change in light beam direction into a direction suitable for an efficient coupling of light into the waveguide by combining optical interaction at a refractive and a reflective surface. This is advantageous as it allows the light to change direction at both these interactions, thus allowing the light incident on the reflective surface to have a direction angularly off-set to the surface of the coupler. As a result from this, the reflective surface may be arranged at an angle larger than 45°. This is an advantage from a manufacturing perspective as the reflective surface may then be created by etching techniques. This simplifies the manufacturing process and allows for providing an optical system for coupling light into a waveguide at a lower cost.

Another important feature is that the optical path changing structure is formed directly in the cladding layer. The cladding layer has multiple purposes. The cladding layer may surround the waveguide along its sides within and/or outside the portion. Thus the cladding layer protects the waveguide. Additionally, the cladding layer may be responsible for achieving internal reflection for light propagating within the waveguide. Internal reflection may be achieved by the cladding layer comprising a material having a refractive index which is lower than the refractive index of the material of the waveguide. It is realised that, by forming the optical path changing structure directly in the cladding layer, a simplified overall structure is obtained. In particular, this allows the optical path changing structure to be monolithically formed. There is thus no need for attachment of separate parts. This allows for a further simplified manufacturing process with the end result of lower price of manufacture.

It should be understood that the first direction is a general direction of light propagation in the portion of the waveguide where the coupler is arranged. This implies that the waveguide is typically not curved throughout the portion. Instead, the waveguide may be linearly shaped within the portion. The waveguide may also be tapered within the portion. This implies that the waveguide may have a cross sectional area that increases in vicinity of the coupler. It is to be noted that the general direction of light propagation is not the same as the optical beam propagation path within the waveguide, a path which is not linear as the light shifts direction at each internal reflection. It is thus understood that the first direction is the direction along the extension of the waveguide within the portion.

By a cladding layer is meant a semiconductor layer formed on the coupler (and usually also around the waveguide) having a refractive index which is lower than the waveguide.

By optical path changing structure is generally meant a structure which is capable of changing the path of an incident light beam. In particular, the optical path changing structure is capable of changing the direction of the incident light beam.

The waveguide may be of the type silicon-on-insulator (SOI). The waveguide may include for example, silicon (Si), polysilicon (poly-Si), a silicon nitride (SiNx), a silicon oxide (SiOx), oxynitride and/or a polymer.

In the above arrangement, the optical path changing structure may be seen as an optical prism, wherein the refractive surface corresponds to a first surface of the optical prism, and wherein the reflective surface corresponds to a second surface of the optical prism.

The refractive index of the cladding layer may be higher than a refractive index of a medium from which light enters the optical path changing structure through the refractive surface.

This implies that the light incident on the refracted surface along the second direction will be refracted to bend off towards the normal of the refractive surface. In other words, the angle formed between the second direction and the normal of the refractive surface is larger than the angle formed between the third direction and the normal of the refractive surface. This allows for reaching an optimum angle of incidence on the grating coupler while still keeping the angle that the reflective surface has with respect to the surface of the grating coupler larger than 45°.

The acute angle formed by the refractive surface may be equal to the acute angle formed by the reflective surface. This provides a symmetric geometry, which is advantageous from a manufacturing perspective. For example, a symmetrical etch may be applied instead of a non-symmetrical etch.

The acute angle formed by the refractive surface and the acute angle formed by the reflective surface may be in the interval 60°-70°. Such angles are possible to manufacture by an etching technique (in contrast to angles below 45°). Still, these angles allows for an optimal or close to optimal coupling efficiency of the optical system. The optimum angle of incidence on the grating coupler is typically around 10-20° dependent on wavelength and grating periods. By providing a refractive surface and a reflective surface with acute angles in the interval 60-70°, such optimum angles of incidence may be obtained.

According to a first group of embodiments, the refractive surface and the reflective surface each extends along an axis which is orthogonal to said normal and said first direction. This is advantageous when designing the optical system for use with a light source which emits light in a direction parallel with the light propagation direction (i.e., the first direction referred to herein) of the waveguide. A further advantage is that the simplified structure, where the two surfaces share a common axis, allows for a simplified manufacturing process.

According to a second group of embodiments, the refractive surface extends along the first direction, and the reflective surface extends along an axis which is orthogonal to said normal and which forms an angle with respect to the first direction. This allows for designing the optical system for use with a light source which emits light in a direction in the plane of the coupler orthogonal to the first direction. This may be advantageous for situations where space is limited and a light source cannot be fitted such that it allows the output of light in a direction parallel with the first direction. Instead, it is possible for the optical path changing structure to receive the light from a side direction. Additionally, the embodiment allows reducing the distance between the mirror and prism, hence reducing optical losses occurring in the optical system.

According to one embodiment, the angle with respect to the first direction is 45°.

It is understood that alternative arrangements of the refractive surface in relation to the reflective surface are possible. For example, the refractive surface may, alternatively, be arranged to extend along an axis which forms an arbitrary angle with respect to the first direction. Similarly, the reflective surface may extend along an axis which forms an arbitrary angle with respect to the first direction.

This would allow an incoming light beam to have an arbitrary direction in a plane orthogonal to the normal. This may be advantageous for situations where space is limited. Custom-tailored solutions may be manufactured for specific platforms.

The optical path changing structure may be an etched structure in the cladding layer. Etching techniques simplify the manufacturing process.

The coupler may be a chirped grating coupler. The chirped grating coupler may comprise a grating structure with a linear chirp. Alternatively, the chirp may be nonlinear, such as e.g. an exponential chirp. The use of a chirped grating coupler is be advantageous as it allows collecting the light from the light source more efficiently when the light has a small spot with large divergence angles.

The reflective surface may be provided with a reflective coating. Such a coating could comprise for example a metal such as e.g. aluminium. Alternatively, the coating could comprise other materials, such as e.g. silicon dioxide. The coating may be a dielectric coating. The coating may comprise more than one layer.

In the embodiments described hereinabove, the reflective properties of the reflective surface are achieved by the optical path changing structure itself, or a coating deposited on it. However, the inventive concepts should not be limited to these embodiments. There are other ways to provide a reflective surface of the optical path changing structure. For example, another object may be used to reflect the light from the second to the third direction. The other object may then be placed in direct contact with the cladding layer reflective surface. The object may have a coating of the same type specified hereinabove.

The waveguide may comprise a reflector which is arranged at a surface of the waveguide which is opposite to the surface of the coupler where the grating structure is formed. This is advantageous as it allows increasing the coupling efficiency by reducing the amount of light penetrating the waveguide on the opposite side of the waveguide of where the coupler is formed.

According to a second aspect, there is provided a diagnostic device comprising the optical system of the first aspect. The diagnostic device may, e.g., be a device which subjects a biological sample to laser light, and detects light that has interacted with the biological sample in order to draw conclusions of the biological sample, such as counting cells in the sample, or identify a disease condition based on the sample.

The second aspect may generally have the same features and advantages as the first aspect. It is further noted that the inventive concepts relate to all possible combinations of features unless explicitly stated otherwise.

Various embodiments will now be described more fully hereinafter with reference to the accompanying drawings. The inventive concepts may, however, be embodied in many different forms and should not be construed as limited to the embodiments set forth herein; rather, these embodiments are provided for thoroughness and completeness, and fully convey the scope of the inventive concepts to the skilled person.

Figure 1:
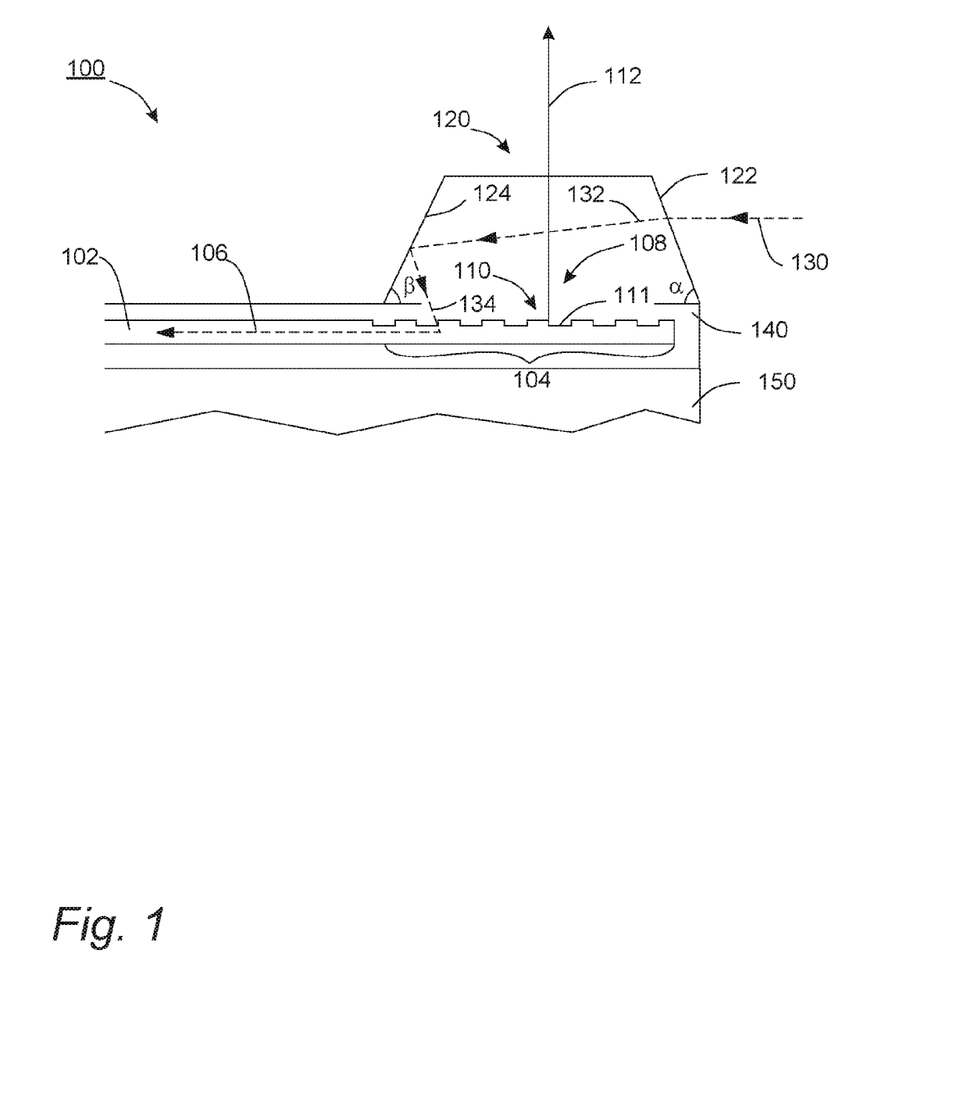
FIG. 1 shows schematically a side view of the optical system according to example embodiments of the present disclosure.

Referring to FIG. 1, an embodiment of an optical system 100 for coupling light into a waveguide is shown schematically in a side view.

The optical system 100 comprises a waveguide 102. The waveguide 102 comprises a portion 104 for guiding light along a first direction 106. The first direction 106 is hence the general propagation direction of light in the waveguide. It is to be understood that the light is not necessarily guided along the first direction 106 throughout the total extension of the waveguide 102. The waveguide 102 may be extending non-linearly at a distance from the portion 104. For example, the waveguide may be arranged to follow a non-linear path in a plane, interconnecting two optical components. However, at the portion 104, where light is to be coupled into the waveguide 102, the waveguide 102 is arranged to direct light along a first direction 106. The waveguide 102 may be a nanophotonic waveguide. The waveguide 102 may be of the type silicon-on-insulator (SOI). The waveguide may include for example, silicon (Si), polysilicon (poly-Si), a silicon nitride (SiNx), a silicon oxide (SiOx), a silicon oxynitride (SiON) and/or a polymer.

The optical system 100 is arranged on top of a semiconductor substrate 150 comprising for example silicon.

The optical system 100 further comprises a coupler 108 for directing light into the waveguide 102. The coupler 108 is arranged at the portion 104 of the waveguide. Here, the coupler 108 is formed on an outer surface 110 of the portion 104 of the waveguide 102. However, alternative arrangements of the coupler 108 are also possible, such as e.g. arranging the coupler 108 inside of the waveguide. The coupler 108 has a surface 110 which has a normal 112 which is transverse, e.g., approximately orthogonal to the propagation direction 106.

The coupler 108 comprises a grating structure 111 arranged to create a diffraction pattern from light incident on the grating structure 111. Such couplers are known as grating couplers. The diffraction pattern will depend on the angle of incidence of the light with respect to the grating (the angle of incidence is the angle with respect to the grating, i.e. the angle formed between the incident light and the normal 112). By matching a diffraction mode of the diffraction pattern with an internal mode of the waveguide 102, light may be efficiently coupled via the grating into the waveguide 102. The grating structure 111 comprises a plurality of recessed and raised portions. According to embodiments, the grating can be a uniform or an apodized or a chirped structure.

The grating structure 111 may have equidistant spacing, also referred to as a grating period, between its raised portions. The grating period is a design parameter which may be set depending on the wavelength of the light, and the angle of incidence obtained with the system. For each wavelength and each angle of incidence on the grating, there is a grating period which optimizes the coupling efficiency. This will be the optimal choice of grating period for a particular wavelength and angle of incidence. The grating structure 111 may alternatively have a non-equidistant spacing between its raised portions. A grating coupler comprising such a grating structure is called a chirped grating coupler. The chirped grating coupler may comprise a grating structure with a linear chirp. Alternatively, the chirp may be nonlinear, such as e.g. an exponential chirp. The use of a chirped grating coupler may allow increasing the collection efficiency especially for situations where the light source has a small light emitting region and the light is emitted with large divergence. Such a light source may be for example a diode laser.

As is well known in the art, the optimum angle of incidence on the grating structure 111, the wavelength of the incident light and the spacing between the raised portions of the grating structure 111 are all interrelated properties. Thus, different designs of the grating structure 111 are possible dependent on the operating wavelength etc.

The coupler in the currently described embodiment comprises a grating structure. It is to be understood, however, that the coupler is not necessarily limited to the configuration shown, and may include alternative configurations capable of directing light in the described manner.

The waveguide 102 is surrounded by a cladding layer 140. The cladding layer 140 may comprise for example, an oxide, in particular $SiO_2$, a siliconoxynitride (SiON), aluminium oxide (AlOx), and/or a polymer. One purpose of the cladding layer 140 is to provide the waveguide 102 with internal surfaces at which total or near total internal reflection may be achieved for light traveling through the waveguide 102. This may be achieved by using a material of the cladding layer 140 with a lower refractive index than that of the material of the waveguide 102.

The optical system 100 further comprises an optical path changing structure 120 formed on the coupler 108. The optical path changing structure 120 has a refractive surface 122 and a reflective surface 124, each forming an acute angle $\alpha$, $\beta$ with respect to the surface 110 of the waveguide 102. By acute angle is meant an angle which is larger than 0° but smaller than 90°. The refractive surface 122 and the reflective surface 124 are planar surfaces. The optical path changing structure 120 is arranged such as to allow light that enters through the refractive surface 122 to refract and thus alter its propagation direction. This may be achieved by the optical path changing structure 120 having a higher refractive index than the surrounding medium. The refractive index of the optical path changing structure 120 is higher than the refractive index of the medium from which light enters the optical path changing structure 120 through the refractive surface 122. For example, if the medium from which light enters the optical path changing structure 120 is air (refractive index n=1.0), a suitable refractive index of the optical path changing structure 120 may be in the interval 1.4-1.5 for light at the wavelength $\lambda$=650 nm. One cladding layer material suitable for the purpose is $SiO_2$ which has a refractive index of n=1.46 at $\lambda$=650 nm.

Specifically, light that enters the optical path changing structure 120 along a second direction 130 which is orthogonal to the normal 112 will be refracted, by the refractive surface 122, such that the light is directed towards the reflective surface 124 along a third direction 132 which is different from the second direction 130. The reflective surface 124 is arranged to reflect the light of the third direction 132 such that it is directed towards the coupler 108 along a fourth direction 134. The angle formed between the fourth direction 134 and the normal 112 is the angle of incidence on the grating 111.

The illustrated coupler 108 has a backfire configuration, which implies that the horizontal component of the fourth direction 134 is opposite to the first direction 106. However, also an end fire configuration would be possible, where the horizontal component of the fourth direction 134 is parallel to the first direction 106. In that case, the first direction 106 in FIG. 1 would be reversed.

The purpose of the optical path changing structure 120 is to provide a light beam at a suitable angle of incidence for coupling the light beam into the waveguide 102. Such a suitable angle is typically within the interval 10°-20°. The acute angle $\alpha$ of the refractive surface 122 and the acute angle $\beta$ of the reflective surface 124 are chosen such that light that propagates along the fourth direction 134 is typically incident on the coupler at the angle of 10-20° to the normal 112.

The acute angle $\alpha$ formed by the refractive surface 122 may be equal to the acute angle $\beta$ formed by the reflective surface 124. Alternatively, the acute angle $\alpha$ formed by the refractive surface 122 may be different from the acute angle $\beta$ formed by the reflective surface 124. The distance between the refractive surface 122 and the reflective surface 124 may be adjusted for optimizing a particular embodiment. The acute angle $\alpha$ formed by the refractive surface 122 and the acute angle $\beta$ formed by the reflective surface 124 are typically in the interval 60-70°. For the example given hereinabove where the surrounding medium is air (n=1.0) and the optical path changing structure 120 has the refractive index n=1.46 at $\lambda$=650 nm, the angles $\alpha$ and $\beta$ of 60° will result in an angle of incidence of the light beam towards to grating structure 111 of 20° with respect to the normal 112.

It should be understood that the inventive concept must not be limited to the described embodiment where the angles are acute. In an alternative embodiment of the invention, the angles are obtuse, and incoming light is refracted towards the top surface of the optical path changing structure where it is reflected either by total internal reflection of by a reflective coating arranged on the top surface. The light may then be reflected directly towards the coupler. Alternatively, the light may be reflected once more in another surface of the optical path changing structure different from the top surface, by total internal reflection or by a reflective coating on said surface, after which the light is directed towards the coupler.

The beam propagation geometry of the embodiment of the optical system 100 illustrated in FIG. 1 is essentially planar as the light beam propagates along directions all coinciding with a common vertical plane (i.e. the plane of the paper in FIG. 1). It should be understood that other geometries are also possible within the scope of the claims. To illustrate this, two embodiments will be discussed with reference to FIGS. 2a-b and 3a-d.

Figure 2A:
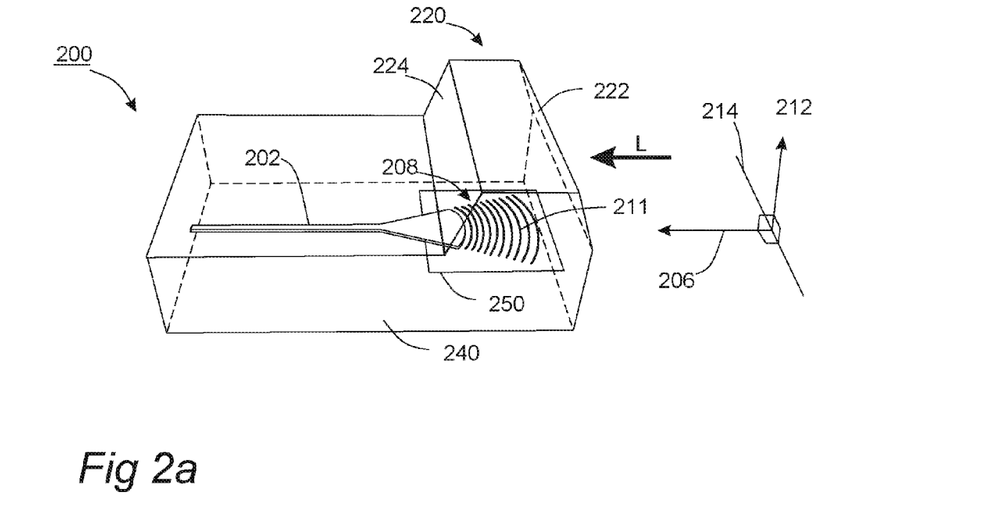
FIG. 2a shows schematically a three-dimensional view of the optical system in a back-fire configuration according to example embodiments of the present disclosure.

The optical system 200 shown in FIG. 2a is following the essentially planar beam geometry. This is useful when the incident light beam is propagating in a direction parallel with the first direction 206 (the light thus enters the optical system 200 from the right in FIG. 2a, as referenced by the arrow L). This beam geometry is realized by providing the refractive surface 222 and the reflective surface 224 such that each extends in a direction 214 which is orthogonal to the normal 212 and the first direction 206.

In more detail, the refractive surface 222 may be seen as a geometrical plane which has two dimensions. In the first dimension, the refractive surface 222 extends along a direction 214 which is parallel to the planar surface of the coupler (i.e. orthogonal to the normal 212), and which is also orthogonal to the first direction 206 (i.e. orthogonal to the propagation direction of light in the waveguide). In the second dimension, the refractive surface 222 extends along a direction which is orthogonal to the direction of the first dimension of the refractive surface 222, and which forms an angle $\alpha$ (see FIG. 1) with respect to the planar surface of the coupler.

Similarly, the reflective surface 224 may be seen as a geometrical plane which has two dimensions. In the first dimension, the reflective surface 224 extends along a direction 214 which is parallel to the planar surface of the coupler (i.e. orthogonal to the normal 212), and which is also orthogonal to the first direction 206 (i.e. orthogonal to the propagation direction of light in the waveguide). In the second dimension, the reflective surface 224 extends along a direction which is orthogonal to the direction of the first dimension of the reflective surface 224, and which forms an angle $\beta$ (see FIG. 1) with respect to the (planar, apart from the grating structure) surface of the coupler.

In FIG. 2a, for clarity, the first direction 206, the normal 212 and the direction 214 have been illustrated to the right of the optical system 200. It should be understood that the refractive surface 222 and the reflective surface 224 thus share at least one direction in space, i.e., direction 214.

The optical system 200 comprises a cladding layer 240 encompassing the waveguide 202 on the surfaces of the waveguide parallel with the propagation direction of light in the waveguide 202. The cladding layer 240 is formed on the grating coupler 208 and thus covers the grating structure 211. The optical path changing structure 220 is formed in the cladding layer 240. Thus, the cladding layer 240 and the optical path changing structure 220 forms different portions of the same material. In other words, the optical path changing structure is monolithically formed in the cladding layer. Specifically, the optical path changing structure 220 is an etched structure in the cladding layer 240.

The optical system 200 further comprises a reflector 250 which is arranged at a surface of the waveguide which is opposite to the surface of the waveguide where the grating coupler 208 is formed. The reflector 250 is used to reflect parts of the diffracted light transmitted through the waveguide 202 back into the waveguide 202 to increase coupling efficiency. The waveguide 202 is tapered to allow improved collection efficiency between the grating coupler 208 and the waveguide 202.

Figure 2B:
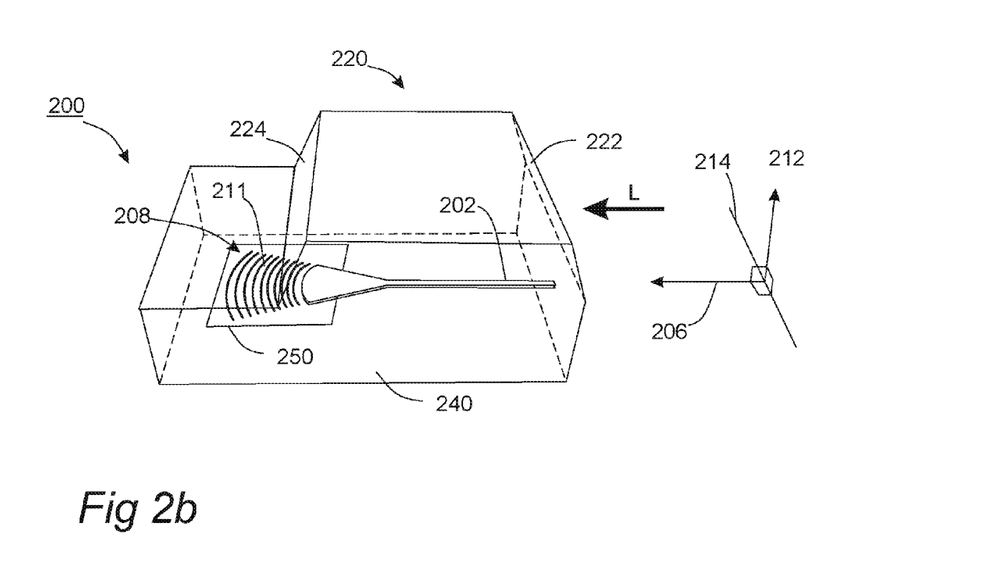
FIG. 2b shows schematically a three-dimensional view of the optical system in an end-fire configuration according to example embodiments of the present disclosure.

The illustrated coupler 208 (FIG. 2a) has a back-fire configuration. However, also an end-fire configuration would be possible, where the coupler 208 instead is arranged to redirect light into a direction which is opposite to that of FIG. 2a. Such an end-fire configuration is shown in FIG. 2b.

Figures 3A, 3B:
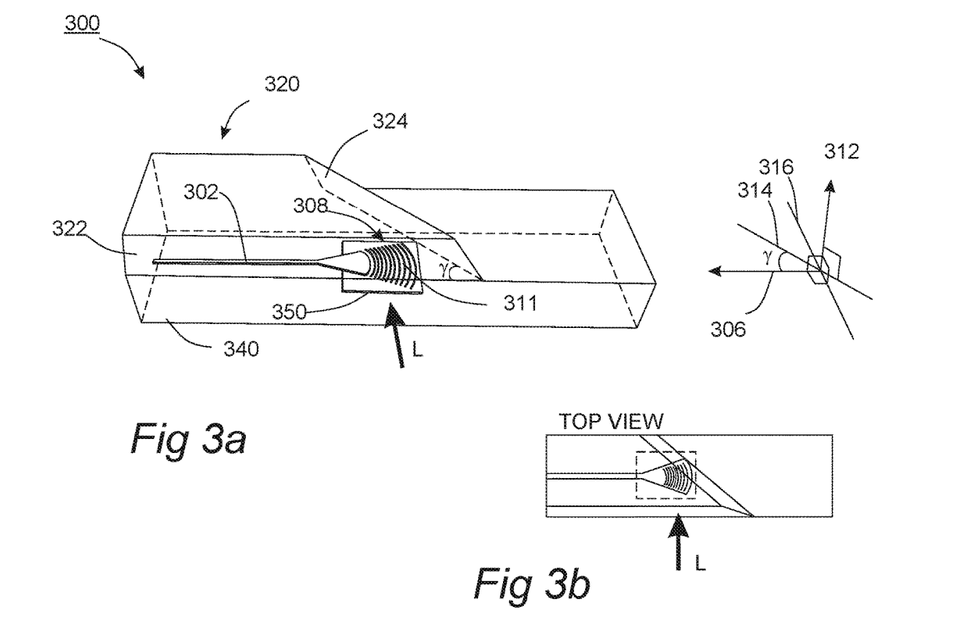

FIG. 3a (and FIG. 3b showing the top view) shows an optical system 300 that does not follow the essentially planar configuration. The optical system 300 is useful when the incident light beam is propagating in a direction perpendicular to the first direction (the light thus enters the optical system 300 from the side in FIG. 3a, as references by the arrow L). The optical system 300 is the same as the optical system 200 in all other respects than the orientation of the refractive surface 322 and the reflective surface 324 of the optical path changing structure 320.

This beam geometry is realized by providing the refractive surface 322 such that it extends along the first direction 306. If the refractive surface 322 is seen as a geometrical plane having two dimensions, the first dimension is thus parallel to the first direction (i.e. parallel to the propagation direction of light in the waveguide). The second dimension of the refractive surface 322 is orthogonal to the first direction 306 and forms an angle (cf. the angle α of FIG. 1) with respect to the surface of the coupler. The reflective surface 324 extends along a direction 314 which is orthogonal to said normal 312 and which forms an angle γ with respect to the first direction 306. If the reflective surface 324 is seen as a geometrical plane having two dimensions, the first dimension thus extends along a direction which is parallel to the surface of the coupler (i.e. orthogonal to the normal 312), and which forms an angle γ with respect to the first direction. Along the second dimension (which is orthogonal to the first dimension) the reflective surface 324 forms an angle with respect to the surface of the coupler (cf. the angle β of FIG. 1).

Light enters the optical system 300 at a direction parallel with the direction 316. In FIG. 3a, for clarity, the first direction 306, the normal 312 and the direction 314 have been illustrated to the right of the optical system 300. The angle γ may e.g. be 45°.

Figures 3C, 3D:
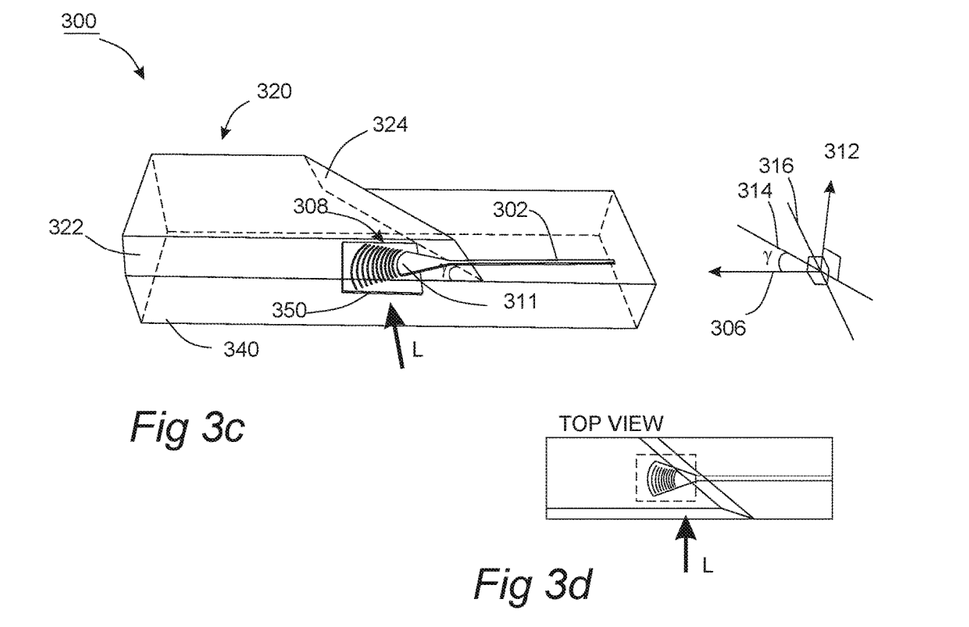
FIG. 3c shows schematically a three-dimensional view of the optical system in an end-fire configuration according to example embodiments of the present disclosure.
FIG. 3d shows schematically a top view of the optical system of FIG. 3c

The illustrated coupler 308 (FIG. 3a) has a back-fire configuration. However, also an end-fire configuration would be possible, where the coupler 308 instead is arranged to redirect light into a direction which is opposite to that of FIG. 3a. Such an end-fire configuration is shown in FIG. 3c (FIG. 3d showing the top view).

Figure 4:
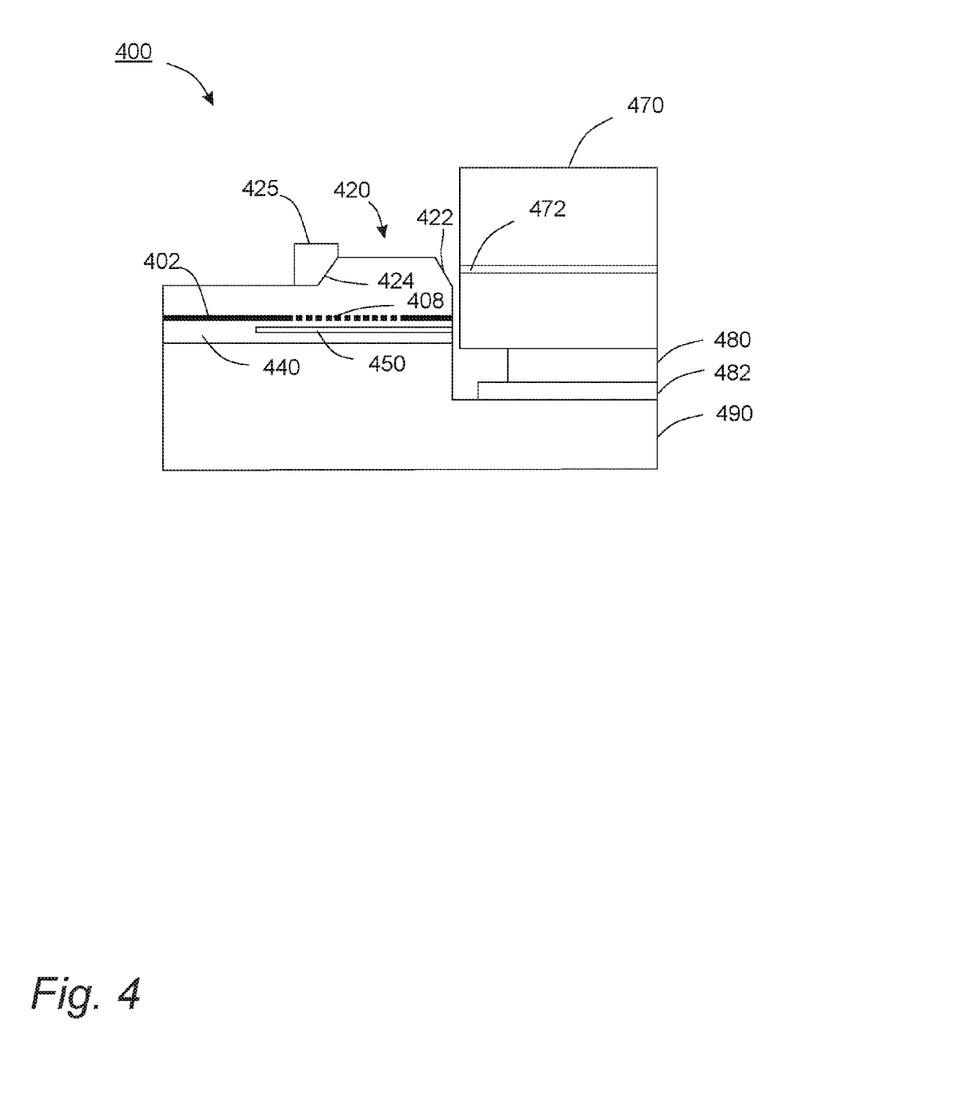
FIG. 4 shows schematically a side view of an optical arrangement comprising an optical system according to example embodiments of the present disclosure.

FIG. 4 shows an example of an optical arrangement 400 comprising an optical system according to one embodiment. The beam geometry is planar, i.e. the same as for the embodiment shown in FIG. 2. The optical system is mounted on top of a substrate 490 which has been manufactured such as to allow at least two horizontal surfaces at different heights. The substrate may comprise silicon. At the lowest height, a laser 470 is mounted on top of a Sn solder 480 layer, and a Ni plate 482. The purpose of these is to attach the laser to the substrate 490. At the higher height, the optical system is mounted, the lower surface of the cladding layer 440 being arranged on the surface of the supporting structure 490. The laser 470 is an edge emitting laser with an active region 472 where stimulated emission occurs. The laser emits a beam incident towards the refractive surface 422 from which it is directed into the waveguide 402 via coupler 408, which is backed by reflector 450, as disclosed hereinabove. The reflective surface is realized by using a metal mirror 425 attached to the cladding layer 440.

Figure 5:
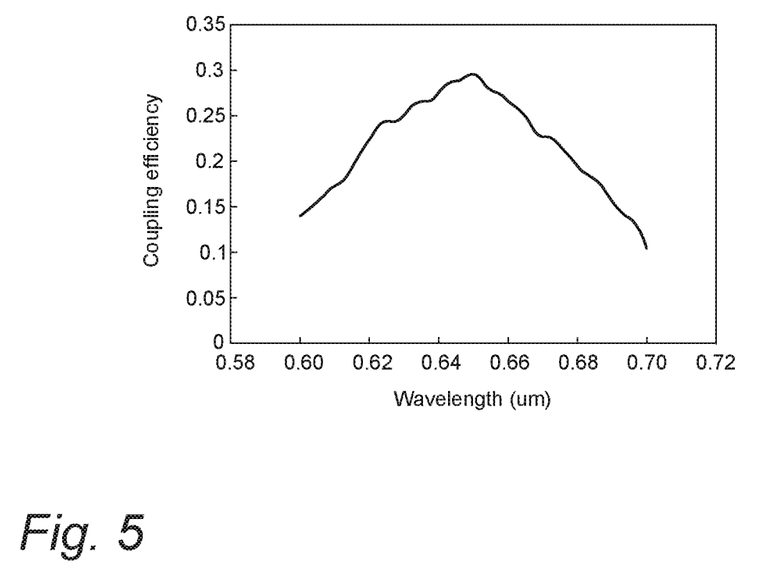
FIG. 5 shows the coupling efficiency as function of wavelength for an optical system according to embodiments of the present disclosure.

FIG. 5 shows the coupling efficiency as a function of wavelength for a particular exemplary embodiment. A waveguide made of silicon nitride was used. Silicon nitride has a refractive index of 1.9 for a wavelength of 650 nm. A cladding layer made of $SiO_2$ was used. $SiO_2$ has a refractive index of 1.46 for a wavelength of 650 nm. The angles α and β of the refractive and reflective surfaces, respectively, were 65°. A bottom mirror, or reflector, was also included to increase the coupling efficiency. With this choice of parameters, the coupling efficiency is about 30% for a wavelength of 650 nm.

The embodiments herein are not limited to the above described examples. Various alternatives, modifications and equivalents may be used. Therefore, this disclosure should not be limited to the specific form set forth herein. This disclosure is limited only by the appended claims and other embodiments than the mentioned above are equally possible within the scope of the claims.

The invention claimed is:

1. An optical system for coupling light into a waveguide, comprising:
   a waveguide having a portion for guiding light along a first direction,
   a coupler arranged at said portion of the waveguide, wherein the coupler has a surface with a grating structure formed therein for directing light into the waveguide, the surface having a normal which is orthogonal to the first direction, and
   a cladding layer embedding the coupler, the cladding layer having an optical path changing structure formed therein, the optical path changing structure having a refractive surface and a reflective surface, each forming an acute angle with respect to the surface of the coupler,
   wherein, for light which enters the optical path changing structure through the refractive surface along a second direction which is orthogonal to said normal, the refractive surface is arranged to refract the light such that it is directed towards the reflective surface along a third direction which is different from the second direction, and
   wherein the reflective surface is arranged to reflect the light of the third direction such that it is directed towards the grating structure of the coupler along a fourth direction.

2. The optical system of claim 1, wherein the optical path changing structure includes an optical prism, wherein the refractive surface corresponds to a first surface of the optical prism, and wherein the reflective surface corresponds to a second surface of the optical prism.

3. The optical system of claim 1, wherein a refractive index of the cladding layer is higher than a refractive index of a medium from which light enters the optical path changing structure through the refractive surface.

4. The optical system of claim 1, wherein the acute angle formed by the refractive surface equal to the acute angle formed by the reflective surface.

5. The optical system of claim 1, wherein the acute angle formed by the refractive surface and the acute angle formed by the reflective surface are in the interval 60-70°.

6. The optical system of claim 1, wherein the refractive surface and the reflective surface each extends along a direction which is orthogonal to said normal and said first direction.

7. The optical system of claim 1, wherein the refractive surface extends along the first direction, and the reflective surface extends along a direction which is orthogonal to said normal and which forms an angle with respect to the first direction.

8. The optical system of claim 7, wherein the angle with respect to the first direction is 45°.

9. The optical system of claim 1, wherein the optical path changing structure is an etched structure in the cladding layer.

10. The optical system of claim 1, wherein the coupler is a chirped grating coupler.

11. The optical system of claim 1, wherein the reflective surface is provided with a reflective coating.

12. The optical system of claim 1, further comprising a reflector disposed on a side of the coupler opposite to the side of the coupler on which the light is received from the reflective surface and arranged to reflect back to the grating structure of the coupler light which passes through the grating structure.

13. A diagnostic device comprising the optical system of claim 1.

* * * * *